(12) United States Patent
Stelzig et al.

(10) Patent No.: US 10,117,810 B2
(45) Date of Patent: *Nov. 6, 2018

(54) DENTAL CEMENT COMPOSITION

(75) Inventors: Simon Stelzig, Constance (DE);
Joachim E. Klee, Radolfzell (DE);
Andreas Facher, Gundetswil (CH);
Christoph Weber, Constance (DE)

(73) Assignee: Dentsply International Inc., York, PA (US)

( * ) Notice: Subject to any disclaimer, the term of this patent is extended or adjusted under 35 U.S.C. 154(b) by 889 days.

This patent is subject to a terminal disclaimer.

(21) Appl. No.: 13/979,806

(22) PCT Filed: Oct. 18, 2011

(86) PCT No.: PCT/EP2011/005238
§ 371 (c)(1),
(2), (4) Date: Oct. 22, 2013

(87) PCT Pub. No.: WO2012/052163
PCT Pub. Date: Apr. 26, 2012

(65) Prior Publication Data
US 2018/0071175 A1    Mar. 15, 2018

(30) Foreign Application Priority Data
Oct. 19, 2010   (EP) ..................... 10013770

(51) Int. Cl.
*A61K 6/083*   (2006.01)
*A61K 6/00*    (2006.01)
*A61K 6/09*    (2006.01)
*C07C 233/09*  (2006.01)
*C07C 233/20*  (2006.01)
*C08F 122/38*  (2006.01)

(52) U.S. Cl.
CPC .......... *A61K 6/0835* (2013.01); *A61K 6/0023* (2013.01); *A61K 6/0091* (2013.01); *A61K 6/09* (2013.01); *C07C 233/09* (2013.01); *C07C 233/20* (2013.01); *C08F 122/385* (2013.01)

(58) Field of Classification Search
CPC .................................................. A61K 6/0835
See application file for complete search history.

(56) References Cited

U.S. PATENT DOCUMENTS

| | | |
|---|---|---|
| 3,655,605 A | 4/1972 | Smith et al. |
| 3,814,717 A | 6/1974 | Wilson et al. |
| 4,016,124 A | 4/1977 | Crisp et al. |
| 4,035,321 A | 7/1977 | Shahidi et al. |
| 4,089,830 A | 5/1978 | Tezuka et al. |
| 4,143,018 A | 3/1979 | Crisp et al. |
| 4,209,434 A | 6/1980 | Wilson et al. |
| 4,317,681 A | 3/1982 | Beede et al. |
| 4,342,677 A | 8/1982 | Muramatsu et al. |
| 4,360,605 A | 11/1982 | Schmitt et al. |
| 4,374,936 A | 2/1983 | Tomioka et al. |
| 4,376,835 A | 3/1983 | Schmitt et al. |
| 4,518,749 A | 5/1985 | Waddill et al. |
| 5,130,347 A | 7/1992 | Mitra |
| 5,154,762 A | 10/1992 | Mitra et al. |
| 6,953,832 B2 | 10/2005 | Moszner et al. |
| 9,603,780 B2* | 3/2017 | Stelzig ............... A61K 6/0023 |
| 9,668,944 B2* | 6/2017 | Stelzig ............... A61K 6/0091 |
| 2003/0232944 A1 | 12/2003 | Molenberg et al. |

FOREIGN PATENT DOCUMENTS

| | | |
|---|---|---|
| DE | 19607641 A1 | 9/1997 |
| DE | 10058829 A1 | 6/2002 |
| DE | 10058830 A1 | 6/2002 |
| EP | 0797972 A2 | 10/1997 |
| EP | 2058318 A1 | 5/2009 |
| JP | 2005065902 A | 3/2005 |

(Continued)

*Primary Examiner* — Michael F Pepitone
(74) *Attorney, Agent, or Firm* — McNees Wallace & Nurick LLC

(57) ABSTRACT

Dental cement composition comprising (i) a particulate filler reactive with a polyacid in a cement reaction; (ii) a water-soluble polymerizable compound of the following formula (1), AXn (1) wherein A is a linker group containing at least n nitrogen atoms and optionally one or more acidic groups, X are moieties containing a polymerizable double bond and forming an amide bond with a nitrogen atom of A, which X may be the same or different and are represented by the following formula (2) wherein $R^1$ and $R^2$ are independent from each other and represent a hydrogen atom, a $C_{1-6}$ alkyl group or a group $—(CH_2)_m—Z$, wherein Z is COOM, $OPO_3M_2$, $PO_3M_2$, $SO_3M$, and M is independently a hydrogen atom or a metal atom, and m is an integer of from 0 to 6, L is a bond or a $C_{1-6}$ alkylene group; and n is an integer of at least 1; provided that at least one X cannot be a (meth)acryl group; and (iii) an initiator system; optionally a polyacidic polymer having polymerizable double bonds; and optionally water.

(2)

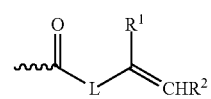

20 Claims, No Drawings

(56) References Cited

FOREIGN PATENT DOCUMENTS

| JP | 2006512466 A | 4/2006 |
|----|--------------|--------|
| WO | 92/21632 A2  | 12/1992 |
| WO | 95/27008 A1  | 10/1995 |
| WO | 00/05182 A1  | 2/2000 |
| WO | 02/41845 A1  | 5/2002 |
| WO | 02/092021 A1 | 11/2002 |
| WO | 03/013444 A1 | 2/2003 |
| WO | 03/035013 A1 | 5/2003 |
| WO | 2008121895 A1 | 10/2008 |

* cited by examiner

DENTAL CEMENT COMPOSITION

FIELD OF THE INVENTION

The present invention relates to a dental cement composition containing a specific water-soluble hydrolysis-stable polymerizable compound. Furthermore, the present invention relates to a process for the preparation of the water-soluble hydrolysis-stable polymerizable compound contained in the dental cement composition according to the present invention. Furthermore, the present invention relates to a novel polymerizable hydrolysis-stable compound useful for a dental cement composition according to the present invention. The present invention also relates to the use of a water-soluble hydrolysis-stable polymerizable compound according to the invention for the preparation of a dental composition. Finally, the present invention relates to a dental composition comprising the water-soluble hydrolysis-stable polymerizable compound according to the invention. The dental cement composition according to the present invention provides improved mechanical properties and handling properties based on a combination of specific setting mechanisms.

BACKGROUND OF THE INVENTION

Dental cements are usually powder liquid systems consisting of linear poly(alkenoic acid)s and reactive ion releasing active glasses. The most common poly(alkenoic acid)s are polymers such as polyacrylic acid or copolymers of acrylic and itaconic acid, acrylic acid and maleic acid and to some degree a copolymer of acrylic acid with methacrylic acid.

In the presence of water, the poly(alkenoic acid) attacks the glass powder whereby metal ions such as calcium, aluminum and strontium are released under formation of intra- and intermolecular salt bridges which crosslink the composition.

Generic cements have a number of important advantages for applications in dentistry such as the virtual absence of an exothermic reaction, no shrinkage during setting, no free monomer in the set composition, high dimensional stability, fluoride release and good adhesion to tooth structure.

Beside these advantageous properties, the main limitation of the glass ionomer cements is their relative lack of strength and low resistance to abrasion and wear. Conventional glass ionomer cements have low flexural strength but high modulus of elasticity, and are therefore very brittle and prone to bulk fracture.

In order to improve the mechanic properties especially flexural strength and fracture toughness numerous investigations were carried out in the last decades, which are directed to the use of amino acids (Z. Ouyang, S. K. Sneckberger, E. C. Kao, B. M. Culbertson, P. W. Jagodzinski, Appl. Spectros 53 (1999) 297 301; B. M. Culbertson, D. Xie, A. Thakur, J. Macromol. Sci. Pure Appl. Chem. A 36 (1999) 681 96), the application of water soluble copolymers using poly(N-vinylpyrrolidone) (D. Xie, B. M. Culbertson, G. J. Wang, J. Macromol. Sci. Pure Appl. Chem. A 35 (1998) 54761), the use of polyacids with narrow molecular weight distribution (DE 100 58 829) and star-like branched polyacids (DE 100 58 830). Further polyacids having a limited molecular mass ranging from 20,000 to 50,000 Da EP 0 797 975) and 1,000 to 50,000 Da (WO 02/41845) were proposed. A further approach was the application of spherical ionomer particles (WO 00/05182).

WO92/21632 discloses a method for treating fluoroaluminum glass with a hydrolyzable polymerizable silane.

WO2008/121895 discloses bioabsorbable elastomeric polymer networks.

DISCLOSURE OF THE INVENTION

It is the problem of the present invention to provide a dental cement composition which has improved mechanical properties while at the same time maintaining advantages for applications in dentistry such a minimal exothermic reaction, no shrinkage during setting, no free monomer in the set composition, high mechanical and dimensional stability during use, and good adhesion to tooth structure.

Moreover, it is the problem of the present invention to provide a water-soluble polymerizable compound which may be incorporated in a dental cement composition for improving mechanical properties, and a process for the preparation thereof.

The present invention relates to dental cement composition comprising
a particulate filler reactive with a polyacid in a cement reaction;
a water-soluble hydrolysis-stable polymerizable compound of the following formula (1),

wherein
A is a linker group containing at least n nitrogen atoms and optionally one or more acidic groups,
X are moieties containing a polymerizable double bond and forming an amide bond with a nitrogen atom of A, which X may be the same or different and are represented by the following formula (2)

wherein
$R^1$ and $R^2$ are independent from each other and represent a hydrogen atom, a $C_{1-6}$ alkyl group or a group $-(CH_2)_m-Z$, wherein Z is COOM, $OPO_3M_2$, $PO_3M_2$, $SO_3M$, and M is independently a hydrogen atom or a metal atom, and m is an integer of from 0 to 6,
L is a single bond or a $C_{1-6}$ alkylene group; and
n is an integer of at least 1;
provided that at least one X cannot be a (meth)acryl group; and
an initiator system;
optionally a polyacidic polymer having polymerizable double bonds; and
optionally water.

The present invention also relates to a process for the preparation of a water-soluble hydrolysis-stable polymerizable compound of the following formula (1),

wherein
A is a linker group containing at least n nitrogen atoms and optionally one or more acidic groups,
X are moieties containing a polymerizable double bond and forming an amide bond with a nitrogen atom of A, which X may be the same or different and are represented by the following formula (2)

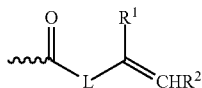
(2)

wherein
R¹ and R² are independent from each other and represent a hydrogen atom, a $C_{1-6}$ alkyl group or a group —$(CH_2)_m$—Z, wherein Z is COOM, $OPO_3M_2$, $PO_3M_2$, $SO_3M$, and M is independently a hydrogen atom or a metal atom, and m is an integer of from 0 to 6;
L is a single bond or a $C_{1-6}$ alkylene group; and
n is an integer of at least 1;
provided that at least one X cannot be a (meth)acryl group; which comprises
a step of an addition or condensation reaction, preferably in a step-growth polymerization, of a mixture containing a diamine and a compound having at least two carboxylic acid groups or an anhydride thereof, optionally in the presence of a compound of the following formula (5) for obtaining a polyamide:

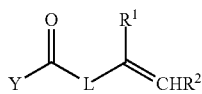
(5)

wherein L, R¹ and R² are as defined in claim 1, and Y is a leaving group or Y forms an intramolecular anhydride group together with a carboxyl group present in R¹ or R² and the adjacent carbonyl group; and
a step of introducing moieties of the formula (2) by reacting the polyamide obtained in step (i) with a compound of formula (5) wherein Y is a leaving group and R¹ and R² are as defined in claim 1; or
a step of reacting a mixture containing a diamine and a compound of formula (5) for obtaining an amide:
and
a step of an addition or condensation reaction, preferably in a step-growth polymerization, of a mixture containing the amide obtained in (iii) and a compound having at least two carboxylic acid groups or an anhydride thereof for obtaining the water-soluble polymerizable compound of the following formula (1)

The present invention also provides a polymerizable compound of the following formula (1a),

$AX_n$ (1a)

wherein
A is a linker group containing at least n nitrogen atoms and optionally one or more acidic groups,
X are moieties containing a polymerizable double bond and forming an amide bond with a nitrogen atom of A, wherein the X, which may be the same or different, are represented by the following formula (2a)

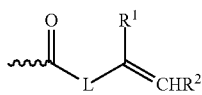
(2a)

wherein
R¹ and R² are independent from each other and represent a hydrogen atom, a $C_{1-6}$ alkyl group or a group —$(CH_2)_m$—Z, wherein Z is COOM, $OPO_3M_2$, $PO_3M_2$, $SO_3M$, and M is independently a hydrogen atom or a metal atom, and m is an integer of from 0 to 6, provided that at least one X cannot be a (meth)acryl group;
L is a single bond or a $C_1$ alkylene group; and
n is an integer of at least 2.

The present invention also provides the use of a compound of formula (1) as defined above, for the preparation of a dental composition.

Finally, the present invention provides a dental composition comprising a water-soluble polymerizable compound of the following formula (1),

$AX_n$ (1)

wherein
A is a linker group containing at least n nitrogen atoms and optionally one or more acidic groups,
X is a moiety containing a polymerizable double bond and forming an amide bond with a nitrogen atom of A, which X may be the same or different and are represented by the following formula (2)

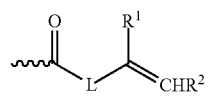
(2)

wherein
R¹ and R² are independent from each other and represent a hydrogen atom, a $C_{1-6}$ alkyl group or a group —$(CH_2)_m$—Z, wherein Z is COOM, $OPO_3M_2$, $PO_3M_2$, $SO_3M$, and M is independently a hydrogen atom or a metal atom, and m is an integer of from 0 to 6;
L is a bond or a $C_{1-6}$ alkylene group; and
n is an integer of at least 1;
provided that at least one X cannot be a (meth)acryl group, and
an initiator system; and optionally
a particulate filler.

The present invention is based on the recognition that a specific water-soluble compound which has improved hydrolysis stability during storage and after curing, is capable of improving the mechanical properties of a dental cement while at the same time maintaining advantages for applications in dentistry such a minimal exothermic reaction, no shrinkage during setting, no free monomer in the set composition, high mechanical and dimensional stability during use, and good adhesion to tooth structure.

The specific water-soluble compounds are hydrolysis-stable. Specifically, the specific water-soluble compound do not contain groups such as ester groups, in the main chain which hydrolyze in aqueous media at pH 3 at room temperature within one month.

DETAILED DESCRIPTION OF PREFERRED EMBODIMENTS

The dental cement composition according to the present invention comprises a particulate filler reactive with a polyacid in a cement reaction. A "particulate filler reactive with a polyacid in a cement reaction" is a powdered metal oxide or hydroxide, mineral silicate, or ion leachable glass or ceramic, that is capable of reacting with an ionomer in the presence of water to form a hydrogel.

Examples of particulate reactive filler materials include materials commonly known in the art of glass-ionomer cements such as calcium or strontium-containing and aluminum-containing materials. Preferably, particulate reactive fillers contain leachable fluoride ions. Specific examples of particulate reactive fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive fillers further include metal oxides such as zinc oxide and magnesium oxide, and ion-leachable glasses, e.g., as described in U.S. Pat. Nos. 3,655,605, 3,814,717, 4,143,018, 4,209,434, 4,360,605 and U.S. Pat. No. 4,376,835.

The particulate reactive filler usually has an average particle size of from 0.005 to 100 μm, preferably of from 0.01 to 40 μm as measured using, for example, by electron microscopy or by using a conventional laser diffraction particle sizing method as embodied by a MALVERN Mastersizer S or MALVERN Mastersizer 2000 apparatus. The particulate reactive filler may be a multimodal particulate reactive filler representing a mixture of two or more particulate fractions having different average particle sizes. The particulate reactive filler may also be a mixture of particles of different chemical composition. In particular, it is possible to use a mixture of a particulate reactive material and a particulate non-reactive material. The particulate reactive filler may be surface modified by a surface modifying agent.

Moreover, the dental cement composition of the present invention comprises a water-soluble hydrolysis-stable polymerizable compound of the following formula (1).

$$AX_n \quad (1)$$

The term "water soluble" means in the context of the present invention that the compound of formula (1) may be dissolved at 25° C. in water at a concentration of at least 1% by weight based on the total weight of water.

In formula (1), A is a linker group containing at least n nitrogen atoms and optionally one or more acidic groups. Preferably, the linker group is a linear or branched monomeric, oligomeric, polymeric or copolymeric group containing nitrogen atoms at the terminal positions for forming an amide bond with a moiety X. A monomeric groups is a low-molecular group having a molecular weight of up to 500. An oligomeric group is a group having a molecular weight of more than 500 to up to 10000 and may be prepared by a polymerization reaction. A polymeric or copolymeric group is a group having a molecular weight of more than 10000 which may be obtained by a polymerization reaction. The step-growth polymerization may involve an addition reaction or a condensation reaction.

Preferably, the linker group is a polyamide group obtainable by a process comprising an addition or condensation reaction of a mixture containing a polyamine of the following formula (3) and a compound of the following formula (4) having at least two carboxylic acid groups, optionally in the presence of a compound of the formula (5):

$$R^3(NHR')_y \quad (3)$$

wherein $R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;

R' represents a hydrogen atom or a substituted or unsubstituted aliphatic or cycloaliphatic hydrocarbon group; and y represents an integer of at least 2;

$$MOOC-R^4-COOM \quad (4)$$

wherein $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, wherein the M which may be the same or different independently represent a hydrogen atom or a metal atom. The metal atom may be an alkali metal or an alkali earth metal. In case of an alkali earth metal, the additional charge on the metal may be neutralized by a further carboxylic acid anion or another anion present in the system.

The addition or condensation reaction may form part of a step-growth polymerization step.

In formula (3), $R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups. If necessary, such groups may be protected by a suitable protecting group.

In formula (3), R' represents a hydrogen atom or a substituted or unsubstituted aliphatic or cycloaliphatic hydrocarbon group. In a preferred embodiment, R' is hydrogen. In a further preferred embodiment, R' is a lower alkyl group having 1 to 6 carbon atoms, more preferably, a lower alkyl group having 1 to 3 carbon atoms. Multiple R' may be the same or different.

In formula (3), y represents an integer of at least 2. Preferably, y is in the range of from 2 to 10 more preferably in the range of from 2 to 5.

In formula (4), $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group and optionally from 1 to 6 functional groups selected from carboxylic acid groups or a salt thereof, hydroxyl groups, thiol groups and amino groups. If necessary, such functional groups may be protected by a suitable protecting group during synthesis of the water-soluble polymerizable compound of the invention.

The carboxylic acid groups of a compound of formula (4) may be present in the form of an anhydride. The anhydride may be in intramolecular anhydride or an intermolecular anhydride. Accordingly, a carboxylic group of a compound of formula (4) may form an anhydride with a carboxylic acid group present in the same molecule or in a further molecule of formula (4). The carboxylic group of a compound of formula (4) may form an anhydride with a further carboxylic acid molecule. Suitable further carboxylic acids may be selected from acetic acid, propanoic acid, butanoic acid and the like.

In formula (5), L, $R^1$ and $R^2$ are as defined above, and Y is a leaving group or Y forms an intramolecular anhydride group together with a carboxyl group present in $R^1$ or $R^2$ and the adjacent carbonyl group.

According to a preferred embodiment, the linker group may be a polyoxyalkylene group containing nitrogen atoms at the terminal positions.

The water soluble polymerizable compound of formula (1) preferably has an average molecular weight of from 300 to 10,000, more preferably 500 to 7000.

In formula (1), X are moieties containing a polymerizable double bond and forming an amide bond with a nitrogen atom of A, which X may be the same or different and are represented by the following formula (2).

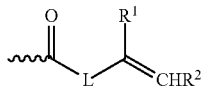

(2)

In formula (2), $R^1$ and $R^2$ are independent from each other and represent a hydrogen atom, a $C_{1-6}$ alkyl group or a group $-(CH_2)_m-Z$, wherein Z is $COOM$, $OPO_3M_2$, $PO_3M_2$, $SO_3M$, and M is independently a hydrogen atom or a metal atom. Preferably, $R^1$ and $R^2$ are independent from each other and represent a hydrogen atom, a $C_{1-6}$ alkyl group or a group $-(CH_2)_m-COOM$, wherein M is a hydrogen atom or a metal atom. In the formula $-(CH_2)_m-Z$, m is an integer of from 0 to 6. Preferably, $R^1$ is single bond or a methyl group. Preferably, $R^2$ is a hydrogen atom or a group $-(CH_2)_m-COOH$, wherein m is 0, 1 or 2.

In formula (2), L is a bond or a $C_{1-6}$ alkylene group, preferably a single bond or a methylene or ethylene group.

In formula (1), n is at least 1. Preferably, n is an integer of at least 1 and less than 10, more preferably 2 to 6.

In a water-soluble polymerizable compound of the formula (1), at least one X cannot be a (meth)acryl group.

The dental cement composition according to the present invention comprises an initiator system. The initiator system may be based on a redox initiator or on a photoinitiator.

In case the dental cement composition contains a redox initiator, the amount of reducing agent and oxidizing agent should be sufficient to provide the desired degree of polymerization. Preferably, the mixed but unset cements of the invention contain a combined weight of about 0.01 to about 10%, more preferably about 0.2 to about 5%, and most preferably about 0.3 to about 3% of the reducing agent and oxidizing agent, based on the total weight (including water) of the mixed but unset cement components. The reducing agent or the oxidizing agent can be microencapsulated as described in U.S. Pat. No. 5,154,762. This will generally enhance shelf stability of the cement parts and if necessary permit packaging both the reducing agent and oxidizing agent together. Water-soluble and water-insoluble encapsulants can be employed. Suitable encapsulating materials include cellulosic materials as cellulose acetate, cellulose acetate butyrate, ethyl cellulose, hydroxymethyl cellulose and hydroxyethyl cellulose being preferred. Other encapsulants include polystyrene, copolymers of polystyrene with other vinylic monomers and polymethylmethacrylate, copolymers of methylmethacrylate with other ethylenically-unsaturated monomers. Preferred encapsulants are ethylcellulose and cellulose acetate butyrate. By varying the choice of encapsulant and the encapsulation conditions, the onset of curing can be tailored to start at times ranging from seconds to minutes. The ratio of amount of encapsulant to activator generally ranges from 0.5 to about 10 and preferably from about 2 to about 6.

Suitable oxidizing agents (initiators) include peroxides such as cumene hydroperoxide, benzoyl peroxide and tert-butyl hydroperoxide, ferric chloride, hydroxylamine (depending upon the choice of reducing agent), perboric acid and its salts, and salts of a permanganate or persulfate anion. Preferred oxidizing agents are peroxides, potassium persulfate, ammonium persulfate and hydrogen peroxide.

Suitable reducing agents (activators) include ascorbic acid, ferrous chloride, ferrous sulfate, hydrazine, hydroxylamine (depending upon the choice of oxidizing agent) oxalic acid, thiourea, benzyl thiourea, and salts of a dithionite or sulfite anion. Preferred reducing agents include ascorbic acid and ferrous sulfate.

A photoinitiator should be capable of promoting polymerization of the polymerizable groups on exposure to light of a suitable wavelength and intensity. The photoinitiator preferably is sufficiently shelf-stable and free of undesirable coloration to permit its storage and use under typical dental conditions. Visible light photoinitiators are preferred. The photoinitiator preferably is water-soluble or water-miscible. Suitable visible light-induced and ultraviolet light-induced initiators include an alpha-diketone (e.g., camphorquinone) with or without additional hydrogen donors (such as sodium benzene sulfinate, amines and amine alcohols). The photoinitiator may be present in an amount sufficient to provide the desired rate of photopolymerization. This amount will be dependent in part on the light source, the thickness of the cement layer to be exposed to radiant energy and the extinction coefficient of the photoinitiator. Preferably, mixed but unset photocurable cements of the invention will contain about 0.01 to about 5%, more preferably from about 0.1 to about 2% photoinitiator, based on the total weight (including water) of the mixed but unset cement components.

The dental cement composition according to the present invention may optionally comprise a polyacidic polymer having polymerizable double bonds. By adding a polyacidic polymer having polymerizable double bonds to the ionomer cement, not only the brittleness may be reduced, but also the mechanical strengths and physical properties such as adhesiveness to a tooth structure are improved.

As used herein, the term "polymer" includes molecules whose backbone is derived from one monomer (viz. a homopolymer) or from two or more monomers (viz., a copolymer). A polymer typically has a weight average molecular weight of at least about 10.000 Da. Polymerizable acids used for preparing polymers useful for glass-ionomer cement systems include alkenoic acids and unsaturated mono-, di- and tricarboxylic acids. Representative alkenoic acids are described, for example, in U.S. Pat. Nos. 4,016, 124, 4,089,830, 3,655,605; 4,143,018; 4,342,677, 4,360, 605, 4,376,835 and U.S. Pat. No. 5,130,347. Specific examples are acrylic acid, methacrylic acid, maleic acid, fumaric acid, itaconic acid, crotonic acid, and derivatives thereof, such as the acid chlorides thereof, the acid anhydrides thereof and chloro or bromo derivatives thereof. Particularly preferred monomers are acrylic acid, itaconic acid and maleic acid, and the chlorides or anhydrides thereof. The pendent carboxylic acid groups of the ionomer must be sufficient in number or percent by weight to bring about the setting or curing reaction in the presence of the modified particulate reactive and/or non-reactive filler.

Polymerizable double bonds as a source of additional covalent crosslinking, which imparts additional strength to the ultimate ionomeric cement composition, may be introduced by reacting a portion of the carboxylic acid groups with a bi-functional monomer. Examples of suitable bi-functional monomers include acryloyl chloride, methacryloyl chloride, vinyl azalactone, allyl isocyanate, 2-hydroxyethylmethacrylate (HEMA), 2-aminoethylmethacrylate, 2-isocyanatoethyl methacrylate (IEM), acrylic acid, methacrylic acid and N-vinylpyrrolidone. Other examples of suitable bi-functional monomers are described in U.S. Pat. Nos. 4,035,321; 5,130,347.

The dental cement composition according to the present invention may optionally comprise water. Water serves as a medium facilitating the transport of ions between the ionomer and the filler, thereby allowing the acid-base chemical cure setting reaction to occur.

To effect cross-linking or additional cross-linking of the cement, one or more comonomers may be included in the cement composition. Suitable comonomers contains at least one polymerizable functional group. Suitable polymerizable functional groups are ethylenically unsaturated groups (e. g. alkenyl groups and preferably vinyl groups). Ethylenically unsaturated groups are polymerisable by a free radical mechanism. Preferred examples are substituted and unsubstituted acrylates, methacrylates, or alkenes.

Methods for preparing generic dental cement compositions are well known. (Crisp et al., "Glass ionomer cement formulations. II. The synthesis of novel polycarboxylic acids," in J. Dent. Res. 59 (6): 1055-1063 (1980)).

A dental cement composition is prepared by mixing the components of the dental cement of the present invention in the presence of water. The components of the cement system can be combined (such as by mixing or blending) in a variety of manners and amounts in order to form the ionomer cements of the present invention.

For example, a concentrated aqueous solution of the water-soluble polymerizable compound, the initiator system and optionally an ionomer may be mixed with the particulate reactive filler and optionally further components at the time of use. The resultant combination allows the setting reaction to begin.

Alternatively, the water-soluble polymerizable compound, the initiator system, the particulate reactive filler and optionally the ionomer are provided as a freeze-dried or lyophilized powdered blend under conditions in which there is not sufficient water to allow the setting reaction to proceed. Such systems can then be combined with water at the time of use in order to begin the setting reaction. Once the setting reaction has begun, the resultant mixture may be formed into its desired shape, followed by curing and allowing the mixture to fully harden.

In general, the concentration of ionomer in water ranges from 25 to 75% by weight, and preferably from 40 to 65 percent. The resultant aqueous solution has a weight ratio of polymer to liquid (polymer:liquid) generally ranging from about 1.5 to 8.

The reaction mixture may also include a modifying agent such as tartaric acid, for adjusting the working time and a setting time, respectively, when preparing the cement as described in U.S. Pat. Nos. 4,089,830, 4,209,434, 4,317,681 and U.S. Pat. No. 4,374,936. In general, an increase in working time results in an increase in setting time as well.

The "working time" is the time between the beginning of the setting reaction when the ionomer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In the setting reaction, the modified particulate reactive filler behaves like a base and reacts with the acidic groups to form a metal polysalt which acts as the binding matrix (Prosser, J. Chem. Tech. Biotechnol. 29: 69-87(1979)). Moreover, due to the presence of polymerizable double bonds, a polymerization reaction takes place. Thereby the bonding of the ionomer to the particulate reactive filler does not only rely on ionic salt bridges which are problematic with regard to the mechanical properties, but also on covalent bonding. The setting reaction is therefore characterized as a dual chemical cure system that proceeds automatically upon mixing the ionomer and modified particulate reactive filler material in the presence of water. The cement sets to a gel-like state within a few minutes and rapidly hardens to develop strength.

The ratio of powder to liquid affects the workability of the mixed ionomer cement systems. Weight ratios higher than 20:1 tend to exhibit poor workability, while ratios below 1:1 tend to exhibit poor mechanical properties, e. g., strength, and hence are not preferred. Preferred ratios are on the order of about 1:3 to about 6:1 and preferably about 1:1 to 4:1.

In case the ionomer cements of the invention may be further cured by a polymerisation reaction, the cements may be polymerized in accordance with known techniques. At least one initiator is required for polymerization methods such as those based on oxidation/reduction reactions and ultraviolet and visible light.

Depending upon the application of the cement and the manner in which polymerization is achieved, various components of the cement compositions may be packaged differently. For example, in the case of a redox-based system, ingredients of the cement composition are divided into two separate packages—the first package containing the copolymer, comonomer, the initiator and water, and the second package containing the reactive filler and the activator. In another embodiment, the first package contains all solid materials (e.g., copolymer, comonomer, reactive filler and if desired, the reducing agent, and the second package contains water and if desired, the initiator. In the case of photo-initiation, the photoinitiator can be included in either the solid (e. g. paste) or liquid parts of the cement.

The cements of the present invention may further contain non-reactive fillers, solvents, pigments, nonvitreous fillers, free radical scavengers, polymerization inhibitors, reactive and nonreactive diluents e.g., 2-hydroxyethyl methacrylate (HEMA), hydroxypropyl methacrylate, bisacrylamides such as N,N'-diethyl-1,3-bisacrylamido-propan (BADEP), 1,3-bisacrylamido-propan (BAP), and 1,3-bisacrylamido-2-ethyl-propan (BAPEN), surfactants (such as to enhance solubility of an inhibitor e. g., polyoxyethylene), coupling agents to enhance reactivity of fillers e.g., 3-(trimethoxysilyl) propyl methacrylate, and rheology modifiers.

Suitable non-reactive fillers may be selected from fillers currently used in dental restorative compositions. The filler should be finely divided and preferably has a maximum particle diameter less than about 100 μm and an average particle diameter less than about 10 μm. The filler may have a unimodal or polymodal (e.g., bimodal) particle size distribution. The filler can be an inorganic material. It can also be a crosslinked organic material that is insoluble in the polymerizable resin, and is optionally filled with inorganic filler. The filler can be radiopaque, radiolucent or non-radiopaque. Examples of suitable non-reactive inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

Suitable solvents or nonreactive diluents include alcohols such as ethanol and propanol. Suitable reactive diluents are alpha,beta unsaturated monomers for providing altered properties such as toughness, adhesion, and set time.

Suitable alpha,beta-unsaturated monomers may be water-soluble, water-miscible or water-dispersible. Water-soluble, water-miscible or water-dispersible acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acrylate]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Furthermore, bisacrylamides such as N,N'-diethyl-1, 3-bisacrylamido-propan (BADEP), 1,3-bisacrylamido-propan (BAP), and 1,3-bisacrylamido-2-ethyl-propan (BAPEN) may also be mentioned.

Mixtures of alpha, beta-unsaturated monomers can be added if desired. Preferably, the mixed but unset cements of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset cement components.

An example of a suitable free radical scavenger is 4-methoxyphenol. An example of a suitable inhibitor is hydroxytoluene or butylated hydroxytoluene (BHT). The amount of inhibitor may be selected from 0.001 to 2% and preferably from 0.02 to 0.5% based on the total weight of the copolymer/comonomer/water mixture.

The process for the preparation of the water-soluble polymerizable compound of the formula (1) according to the present invention comprises a step (i) of an addition or condensation reaction, preferably in a step-growth polymerization, of a mixture containing a diamine and a compound having at least two carboxylic acid groups or an anhydride thereof, optionally in the presence of a compound of the following formula (5) for obtaining a polyamide:

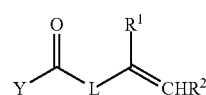

(5)

wherein L, $R^1$ and $R^2$ are as defined above, and Y is a leaving group or Y forms an intramolecular anhydride group together with a carboxyl group present in $R^1$ or $R^2$ and the adjacent carbonyl group, The process further comprises a step (ii) of introducing moieties of the formula (2) by reacting the polyamide obtained in step (i) with a compound of formula (5) wherein Y is a leaving group and $R^1$ and $R^2$ are as defined in claim 1.

Alternatively, the process for the preparation of the water-soluble polymerizable compound of the formula (1) according to the present invention comprises a step (iii) of reacting a mixture containing a diamine and a compound of formula (5) for obtaining an amide and a step (iv) of an addition or condensation reaction, preferably in a step-growth polymerization, of a mixture containing the amide obtained in (iii) and a compound having at least two carboxylic acid groups or an anhydride thereof for obtaining the water-soluble polymerizable compound of the formula (1).

Preferably, the diamine is a compound of the formula (3), $R^3(NHR')_y$, wherein $R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups; R' represents a hydrogen atom or a substituted or unsubstituted aliphatic or cycloaliphatic hydrocarbon group; and y represents an integer of at least 2.

In the process according to the present invention, the compound having at least two carboxylic acid groups is preferably a compound of formula (4), $MOOC-R^4-COOM$, wherein $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, and wherein M, which may be the same or different independently represent a hydrogen atom or a metal atom.

In the process according to the present invention, the compound of formula (5) is preferably itaconic acid or a lactone or a carboxylic anhydride thereof.

In a preferred embodiment, the polymerizable compound of the present invention is a compound of the formula (1a), $AX_n$, wherein A is a linker group containing at least n nitrogen atoms and optionally one or more acidic groups, X are moieties containing a polymerizable double bond and forming an amide bond with a nitrogen atom of A, wherein the X, which may be the same or different, are represented by the following formula (2a)

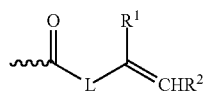

(2a)

wherein
$R^1$ and $R^2$ are independent from each other and represent a hydrogen atom, a $C_{1-6}$ alkyl group or a group $-(CH_2)_m-Z$, wherein Z is COOM, $OPO_3M_2$, $PO_3M_2$, $SO_3M$, and M is independently a hydrogen atom or a metal atom, preferably a group $-(CH_2)_m-COOM$, wherein M is a hydrogen atom or a metal atom, and m is an integer of from 0 to 6, provided that at least one X cannot be a (meth)acryl group; L is a bond or a $C_{1-6}$ alkylene group; and n is an integer of at least 2.

A compound of formula (1) or (1a) according to the present invention may be use for the preparation of a dental composition. Specifically, the dental composition may comprise the water-soluble polymerizable compound of the formula (1) or (1a), an initiator system, and optionally a particulate filler. The dental composition may be a dental adhesive composition or a dental composite composition.

The invention will now be further illustrated by the following Examples. All percentages refer to percentages by weight unless stated otherwise.

EXAMPLE 1

Preparation of a polymerizable compound of formula (1):

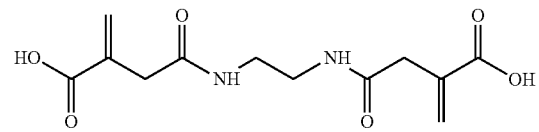 [SMILES: C=C(CC(=O)NCCNC(=O)CC(=C)C(=O)O)C(=O)O]

0.01 mol of ethylendiamine (CAS: 107-15-3) were dissolved in 15 mL chloroform. 0.021 mol itaconic acid anhydride are slurried in 7.5 mL chloroform and slowly added dropwise to the solution of the diamine. After completion of the dropwise addition, the reaction mixture is refluxed for 24 h. The solid obtained is filtered and washed with acetone (50 mL) and dried in vacuo. 2.2 g of a fine particulate white powder are obtained.

IR: ν (in $cm^{-1}$)=3311, 1682, 1647, 1630, 1544
$^1$H-NMR (DMSO-$d_6$, 400 MHz)=6,093/5,774 (d, 2H), 5,637/5,460 (d, 2H), 3,025/3,130/3,068 (s, 8H)

EXAMPLE 2

Preparation of a water-soluble polymerizable compound of formula (1):

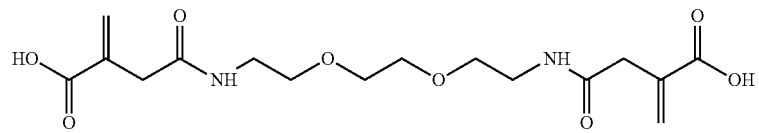 [SMILES: C=C(CC(=O)NCCOCCOCCNC(=O)CC(=C)C(=O)O)C(=O)O]

0.01 mol of 2,2'-(ethylenedioxy)bis(ethylamine) (CAS: 929-59-9) were dissolved in 15 mL chloroform. 0.021 mol itaconic acid anhydride are slurried in 7.5 mL chloroform and slowly added dropwise to the solution of the diamine. After completion of the dropwise addition, the reaction mixture is refluxed for 24 h. The solid obtained is filtered and washed with ethyl acetate (50 mL) and dried in vacuo. 1.7 g of a white solid are obtained.

IR: ν (in cm$^{-1}$)=3310, 1680, 1642, 1628, 1135

$^1$H-NMR (D$_2$O, 400 MHz)=6,254 (s, 2H), 5,754 (s, 2H), 3,553 (s, 4H), 3,503 (tr, 4H, $^3$J=5.2 Hz), 3,283 (tr, 4H, $^3$J=5.2 Hz), 3,185 (s, 4H) ppm.

EXAMPLE 3

Macromonomer 1

0.022 mol (1.32 g) ethylene diamine (CAS: 107-15-3) are dissolved in 4 mL DMSO. 0.010 mol (1.98 g) butane tetracarboxylic acid dianhydride is dissolved in 18 mL DMSO. Both solutions are simultaneously added dropwise to a flask during a predetermined amount of time. BHT is added to the mixture as a stabilizer. The resulting reaction mixture is stirred at 40° C. for 24 h. Subsequently, the 0.022 mol (2.47 g) itaconic acid anhydride (CAS: 2170-03-8) dissolved in 5 mL DMSO is added to the reaction mixture. The reaction solution is stirred for further 72 h at room temperature. Subsequently, the product is precipitated by using a suitable solvent (ethyl acetat, diethy lether, tert.-butylmethyl ether or acetone) and the resulting precipitate is dried.

Calculated degree of polymerization (end group analysis, NMR): n̄≈9.

IR: ν (in cm$^{-1}$)=3309, 3082, 2941, 1710, 1628, 1542

$^1$H-NMR (DMSO-d$_6$, 400 MHz)=12.352 (s, COOH), 8.018-7.807 (m, CONH), 6.111+5.657 (CH$_2$CCH$_3$COO, vinylic protons), 3.079-2.781 (m, backbone), 2.509-2.173 (m, backbone) ppm.

The product obtained is soluble in water in a weight ratio of product/water=1:1.

EXAMPLE 4

Macromonomer 2

0.011 mol (0.66 g) ethylene diamine (CAS: 107-15-3) are dissolved in 4 mL DMSO. 0.010 mol (1.98 g) butane tetracarboxylic acid dianhydride is dissolved in 18 mL DMSO and 0.003 mol (0.28 g) maleinic acid anhydride (CAS: 108-31-6) is added thereto. Both solutions are simultaneously added dropwise to a flask during a predetermined amount of time. BHT is added to the mixture as a stabilizer. The resulting reaction mixture is stirred at room temperature for 16 h. Subsequently, the product is precipitated by using a suitable solvent (ethyl acetat, diethy lether, tert.-butylmethyl ether or acetone) and the resulting precipitate is dried.

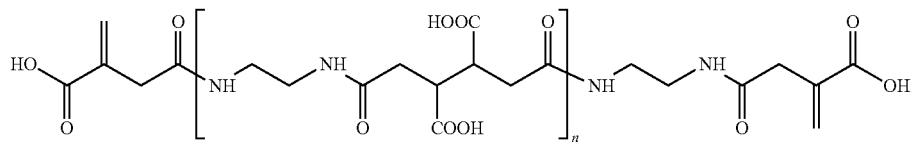

Calculated degree of polymerization (end group analysis, NMR): n̄≈10.

IR: ν (in cm$^{-1}$)=3288, 3076, 2919, 1714, 1648, 1542

$^1$H-NMR (DMSO-d$_6$, 400 MHz)=12.544 (s, COOH), 9.016-8.917+8.022-7.810 (m, CONH), 6.388-6.357+6.242-6.210 (m, CH$_2$CCH$_3$COO, vinylic protons), 3.200-2.718 (m, backbone), 2.509-2.179 (m, backbone) ppm.

The product obtained is soluble in water in a weight ratio of product/water=1:1.

EXAMPLE 5

Formulation Examples

In the following formulation examples, the parts by weight as indicated of a surface treated aluminosilicate glass (d$_{50}$=1.7 μm) are mixed with 1.0 part of a liquid, respectively.

The biaxial flexural strength is measured as follows. In general, samples were stored at 37° C. and at >95% humidity for one hour immediately after preparation, then stored in water at 37° C. for a further 23 hours, before being tested. The biaxial flexural strength values given were measured on discs 20 mm diameter and 1 mm thick, with a supporting knife edge ring support of 15 mm diameter and a pin diameter of 3 mm. The strength values were measured using a Zwick universal testing machine and are reported in MPa. The method is described, for example, in ASTM F 394, and by Wiliams, Billington and Pearson in Dental Materials 2002, July, 18 (5), 376-379.

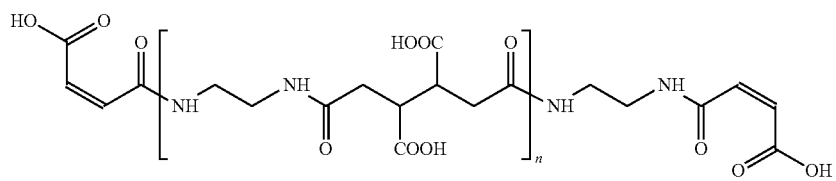

The liquids are further described in the following.
Formulation 1:

| 25.00 wt.-% | HEMA modified polyacrylic acid, |
| 25.10 wt.-% | 2-N,N'-bisacrylamido-N,N'-diethyl-1,3-propane, |
| 4.70 wt.-% | UDMA (Urethandimethacrylat-Resin, CAS: 105883-40-7), |
| 5.00 wt.-% | tartaric acid, |
| 5.00 wt.-% | macromonomer 1, |
| 34.60 wt.-% | water, |
| 0.28 Gew.-% | camphor quinone, and |
| 0.32 Gew.-% | 4-N,N'-dimethylaminobenzonitrile. |

After homogeneously mixing the above components to provide a liquidcomposition, 3.0 parts of the glass are added and mixed, and the sample bodies are irradiated from both sides for the determination of the biaxial flexural strength. After curing the biaxial flexural strength was determined to be 69.24±6.36 MPa.

Formulation 2

| 25.00 wt.-% | HEMA modified polyacrylic acid, |
| 25.10 wt.-% | 2-N,N'-bisacrylamido-N,N'-diethyl-1,3-propane, |
| 4.70 wt.-% | UDMA (Urethandimethacrylat-Resin, CAS: 105883-40-7), |
| 5.00 wt.-% | tartaric acid, |
| 5.00 wt.-% | macromonomer 2, |
| 34.60 wt.-% | water, |
| 0.28 Gew.-% | camphor quinone, and |
| 0.32 Gew.-% | 4-N,N'-dimethylaminobenzonitrile |

After homogeneously mixing the above components to provide a liquidcomposition, 3.0 parts of the glass are added and mixed, and the sample bodies are irradiated from both sides for the determination of the biaxial flexural strength. After curing the biaxial flexural strength was determined to be 71.28±7.66 MPa.

The invention claimed is:

1. A dental cement composition comprising
   (i) a particulate filler reactive with a polyacid in a cement reaction;
   (ii) a water-soluble hydrolysis-stable polymerizable compound of the following formula (1), $$AX_n \quad (1)$$

wherein
   A is a linker group containing at least n nitrogen atoms and optionally one or more acidic groups,
   X are moieties containing a polymerizable double bond and forming an amide bond with a nitrogen atom of A, which X may be the same or different and are represented by the following formula (2)

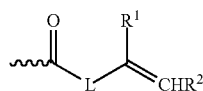
   (2)

wherein
   $R^1$ and $R^2$ are independent from each other and represent a hydrogen atom, a $C_{1-6}$ alkyl group or a group $-(CH_2)_m-Z$, wherein Z is selected from the group consisting of COOM, $OPO_3M_2$, $PO_3M_2$, and $SO_3M$, wherein M is independently a hydrogen atom or a metal atom, and m is an integer of from 0 to 6, L is a bond or a $C_{1-6}$ alkylene group; and
   n is an integer of at least 1;
   provided that at least one X cannot be a (meth)acryl group; and
   (iii) an initiator system;
   (iii) optionally a polyacidic polymer having polymerizable double bonds; and
   (iv) optionally water.

2. The dental cement composition according to claim 1, wherein the linker group is a linear or branched monomeric, oligomeric, polymeric or copolymeric group containing nitrogen atoms at the terminal positions for forming an amide bond with a moiety X.

3. The dental cement composition according to claim 1, wherein the linker group is a polyamide group obtained by a process comprising the step of an addition or condensation reaction of a mixture containing a diamine of the following formula (3) and a compound of the following formula (4) having at least two carboxylic acid groups, said carboxylic acid groups may be present in the form of an anhydride, optionally in the presence of a compound of the following formula (5):

$$R^3(NHR')_y \quad (3)$$

wherein
   $R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;
   R' represents a hydrogen atom or a substituted or unsubstituted aliphatic or cycloaliphatic hydrocarbon group; and
   y represents an integer of at least 2;

$$MOOC-R^4-COOM \quad (4)$$

wherein $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, wherein the M which may be the same or different independently represent a hydrogen atom or a metal atom;

   (5)

wherein L, $R^1$ and $R^2$ are as defined in claim 1, and Y is a leaving group or Y forms an intramolecular anhydride group together with a carboxyl group present in $R^1$ or $R^2$ and the adjacent carbonyl group.

4. The dental cement composition according to claim 2, wherein the linker group is a polyoxyalkylene group containing nitrogen atoms at the terminal positions.

5. The dental cement composition according to claim 1, wherein the water-soluble hydrolysis-stable polymerizable compound of formula (1) has an average molecular weight of from 300 to 10,000.

6. The dental cement composition according to claim 1, wherein n is at least 2.

7. A process for the preparation of a water-soluble hydrolysis-stable polymerizable compound of the following formula (1), $$AX_n \qquad (1)$$

wherein
A is a linker group containing at least n nitrogen atoms and optionally one or more acidic groups,
X are moieties containing a polymerizable double bond and forming an amide bond with a nitrogen atom of A, which X may be the same or different and are represented by the following formula (2)

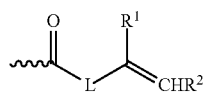

(2)

wherein
$R^1$ and $R^2$ are independent from each other and represent a hydrogen atom, a $C_{1-6}$ alkyl group or a group $-(CH_2)_m-Z$, wherein Z is selected from the group consisting of COOM, $OPO_3M_2$, $PO_3M_2$, and $SO_3M$, wherein M is independently a hydrogen atom or a metal atom, wherein M is a hydrogen atom or a metal atom, and m is an integer of from 0 to 6;
L is a bond or a $C_{1-6}$ alkylene group; and
n is an integer of at least 1;
provided that at least one X cannot be a (meth)acryl group;
which comprises
(i) a step of an addition or condensation reaction of a mixture containing a diamine and a compound having at least two carboxylic acid groups or an anhydride thereof, optionally in the presence of a compound of the following formula (5) for obtaining a polyamide:

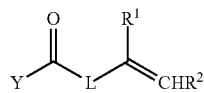

(5)

wherein Y is a leaving group or Y forms an intramolecular anhydride group together with a carboxyl group present in $R^1$ or $R^2$ and the adjacent carbonyl group; and
(ii) step of introducing moieties of the formula (2) by reacting the polyamide obtained in step (i) with a compound of formula (5) wherein Y is a leaving group; or
(iii) a step of reacting a mixture containing a diamine and a compound of formula (5) for obtaining an amide; and
(iv) a step of an addition or condensation reaction of a mixture containing the amide obtained in (iii) and a compound having at least two carboxylic acid groups or an anhydride thereof for obtaining the water-soluble hydrolysis-stable polymerizable compound of formula (1).

8. The process according to claim 7, wherein the diamine is a compound of the formula (3), $$R^3(NHR')_y \qquad (3)$$

wherein
$R^3$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;
R' represents a hydrogen atom or a substituted or unsubstituted aliphatic or cycloaliphatic hydrocarbon group; and
y represents an integer of at least 2.

9. The process according to claim 7, wherein the compound having at least two carboxylic acid groups is a compound of formula (4), $$MOOC-R^4-COOM \qquad (4)$$

wherein $R^4$ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, and wherein the M, which may be same or different, independently represent a hydrogen atom or a metal atom.

10. The process according to claim 7, wherein the compound of formula (5) is itaconic acid or a lactone or a carboxylic anhydride thereof.

11. A hydrolysis-stable polymerizable compound of the following formula (1a), $$AX_n \qquad (1a)$$

wherein
A is a linker group containing at least n nitrogen atoms and optionally one or more acidic groups,
X are moieties containing a polymerizable double bond and forming an amide bond with a nitrogen atom of A, wherein the X, which may be the same or different, are represented by the following formula (2a)

(2a)

wherein
$R^1$ and $R^2$ are independent from each other and represent a hydrogen atom, a $C_{1-6}$ alkyl group or a group $-(CH_2)_m-Z$, wherein Z is selected from the group consisting of COOM, $OPO_3M_2$, $PO_3M_2$, and $SO_3M$, wherein M is independently a hydrogen atom or a metal atom, and m is an integer of from 0 to 6, provided that at least one X cannot be a (meth)acryl group;
L is a bond or a $C_{1-6}$ alkylene group; and
n is an integer of at least 2.

12. A dental composition comprising
a water-soluble hydrolysis-stable polymerizable compound of the following formula (1), $$AX_n \qquad (1)$$

wherein
A is a linker group containing at least n nitrogen atoms and optionally one or more acidic groups, X are moieties containing a polymerizable double bond and forming an amide bond with a nitrogen atom of A, which X may be the same or different and are represented by the following formula (2)

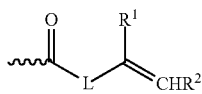  (2)

wherein
R₁ and R₂ are independent from each other and represent a hydrogen atom, a $C_{1-6}$ alkyl group or a group —$(CH_2)_m$—Z, wherein Z is selected from the group consisting of COOM, $OPO_3M_2$, $PO_3M_2$, and $SO_3M$, wherein M is independently a hydrogen atom or a metal atom, and m is an integer of from 0 to 6,
L is a bond or a $C_{1-6}$ alkylene group; and
n is an integer of at least 1;
provided that at least one X cannot be a (meth)acryl group.

13. A dental composition comprising
(i) a water-soluble hydrolysis-stable polymerizable compound of the following formula (1), $AX_n$  (1)

wherein
A is a linker group containing at least n nitrogen atoms and optionally one or more acidic groups,
X is a moiety containing a polymerizable double bond and forming an amide bond with a nitrogen atom of A, which X may be the same or different and are represented by the following formula (2)

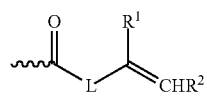  (2)

wherein
R¹ and R² are independent from each other and represent a hydrogen atom, a $C_{1-6}$ alkyl group or a group —$(CH_2)_m$—Z, wherein Z is selected from the group consisting of COOM, $OPO_3M_2$, $PO_3M_2$, and $SO_3M$, wherein M is independently a hydrogen atom or a metal atom, and m is an integer of from 0 to 6;
L is a bond or a $C_{1-6}$ alkylene group; and
n is an integer of at least 1;
provided that at least one X cannot be a (meth)acryl group, and
(ii) an initiator system; and optionally
(iii) a particulate filler.

14. The dental composition according to claim 13, which is a dental adhesive composition or a dental composite composition.

15. The dental cement composition according to claim 2, wherein the linker group is a polyamide group obtained by a process comprising the step of an addition or condensation reaction of a mixture containing a diamine of the following formula (3) and a compound of the following formula (4) having at least two carboxylic acid groups, said carboxylic acid groups may be present in the form of an anhydride, optionally in the presence of a compound of the following formula (5):

  (3)

wherein
R³ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;
R' represents a hydrogen atom or a substituted or unsubstituted aliphatic or cycloaliphatic hydrocarbon group; and
y represents an integer of at least 2;

  (4)

wherein R⁴ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, wherein the M which may be the same or different independently represent a hydrogen atom or a metal atom;

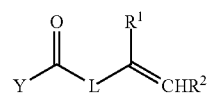  (5)

wherein Y is a leaving group or Y forms an intramolecular anhydride group together with a carboxyl group present in R¹ or R² and the adjacent carbonyl group.

16. The process according to claim 8,
wherein the compound having at least two carboxylic acid groups is a compound of formula (4),

  (4)

wherein R⁴ represents a $C_{1-20}$ straight-chain, branched, cyclic or aromatic hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, and wherein the M, which may be same or different, independently represent a hydrogen atom or a metal atom.

17. The process according to claim 8,
wherein the compound of formula (5) is itaconic acid or a lactone or a carboxylic anhydride thereof.

18. The process according to claim 9,
wherein the compound of formula (5) is itaconic acid or a lactone or a carboxylic anhydride thereof.

19. The dental cement composition according to claim 2, wherein the water-soluble hydrolysis-stable polymerizable compound of formula (1) has an average molecular weight of from 300 to 10,000.

20. The dental cement composition according to claim 3, wherein the water-soluble hydrolysis-stable polymerizable compound of formula (1) has an average molecular weight of from 300 to 10,000.

* * * * *